(12) United States Patent
Horsewood

(10) Patent No.: US 8,124,367 B2
(45) Date of Patent: Feb. 28, 2012

(54) DEVICE FOR APPLYING A DETECTOR REAGENT TO THE SKIN FOR MEASURING CHOLESTEROL

(75) Inventor: Peter Horsewood, Dundas (CA)

(73) Assignee: Miraculins, Inc., Winnipeg, Manitoba (CA)

( * ) Notice: Subject to any disclaimer, the term of this patent is extended or adjusted under 35 U.S.C. 154(b) by 771 days.

(21) Appl. No.: 11/817,293

(22) PCT Filed: Feb. 28, 2006

(86) PCT No.: PCT/CA2006/000293
§ 371 (c)(1),
(2), (4) Date: Oct. 20, 2008

(87) PCT Pub. No.: WO2006/089431
PCT Pub. Date: Aug. 31, 2006

(65) Prior Publication Data
US 2009/0110641 A1    Apr. 30, 2009

Related U.S. Application Data

(60) Provisional application No. 60/656,381, filed on Feb. 28, 2005.

(51) Int. Cl.
*C12Q 1/60* (2006.01)
(52) U.S. Cl. ............................. 435/11; 422/56
(58) Field of Classification Search .................. 435/11; 422/56
See application file for complete search history.

(56) References Cited

U.S. PATENT DOCUMENTS

| | | | |
|---|---|---|---|
| 4,071,318 A | 1/1978 | Lam | |
| 4,458,686 A | 7/1984 | Clark, Jr. | |
| 4,805,529 A * | 2/1989 | Becher | 101/334 |
| 5,318,894 A | 6/1994 | Pugia | |
| 5,340,539 A | 8/1994 | Allen et al. | |
| 5,489,510 A * | 2/1996 | Lopukhin et al. | 435/7.1 |
| 5,587,295 A * | 12/1996 | Lopukhin et al. | 435/11 |
| 5,726,013 A | 3/1998 | Clark | |
| 6,365,363 B1 * | 4/2002 | Parfenov et al. | 435/11 |
| 6,420,181 B1 | 7/2002 | Novak | |
| 6,787,366 B1 | 9/2004 | Novak | |
| 7,238,494 B2 * | 7/2007 | Horsewood et al. | 435/11 |
| 2005/0227369 A1 | 10/2005 | Richardson et al. | |
| 2005/0272112 A1 | 12/2005 | Horsewood et al. | |

FOREIGN PATENT DOCUMENTS

| | | | |
|---|---|---|---|
| WO | 0111359 | | 2/2001 |
| WO | WO 01/11359 | * | 2/2001 |

OTHER PUBLICATIONS

Zawydiwski R. et al. A Novel Test for the Measurement of Skin Cholesterol. Clinical Chemistry 47(7)1302-1304, Jul. 2001.*
H. Bouissou et al., Ann. Biol. Clin. vol. 40, pp. 364-365, 1982.
Y.P. Nikitin et al., Kardiologiia, II, pp. 48-51, 1987.

* cited by examiner

*Primary Examiner* — Ralph Gitomer
(74) *Attorney, Agent, or Firm* — Caesar, Rivise, Bernstein, Cohen & Pokotilow, Ltd.

(57) ABSTRACT

The present invention provides a method and apparatus for non-invasive measurement of skin cholesterol. More particularly, one aspect of the invention provides for a device to apply a detector reagent to a selected area of skin. Another aspect of the invention provides for an indicator device to produce a visual change corresponding to the amount of detector reagent that is bound in the skin. The method and apparatus of this invention typically do not require any instrumentation for certain embodiments, allowing the invention to be suitable for self-testing, for example, but not limited to, in the home environment. As such the invention is particularly useful to allow individuals to assess their risk of atherosclerosis and related vascular diseases.

20 Claims, 6 Drawing Sheets

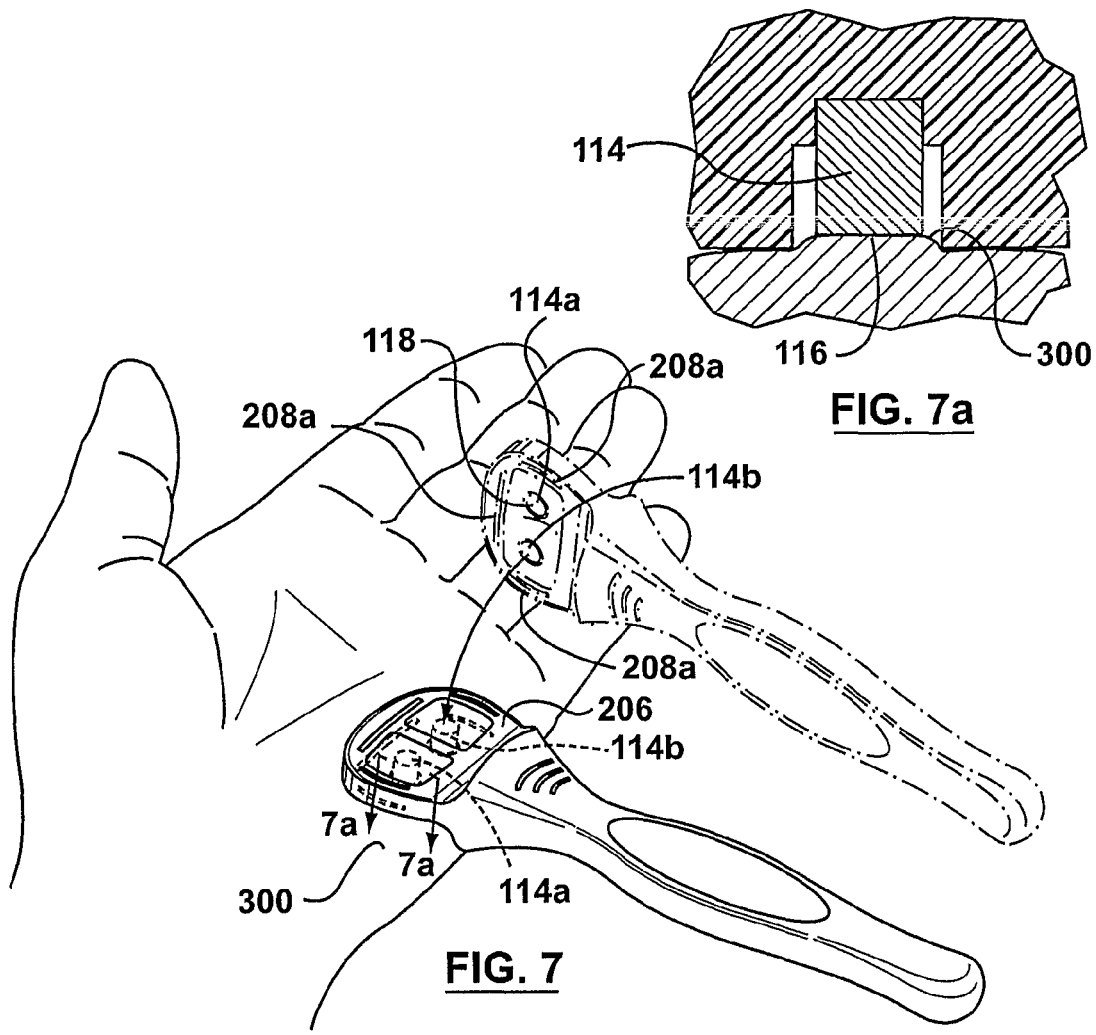
FIG. 7a
FIG. 7
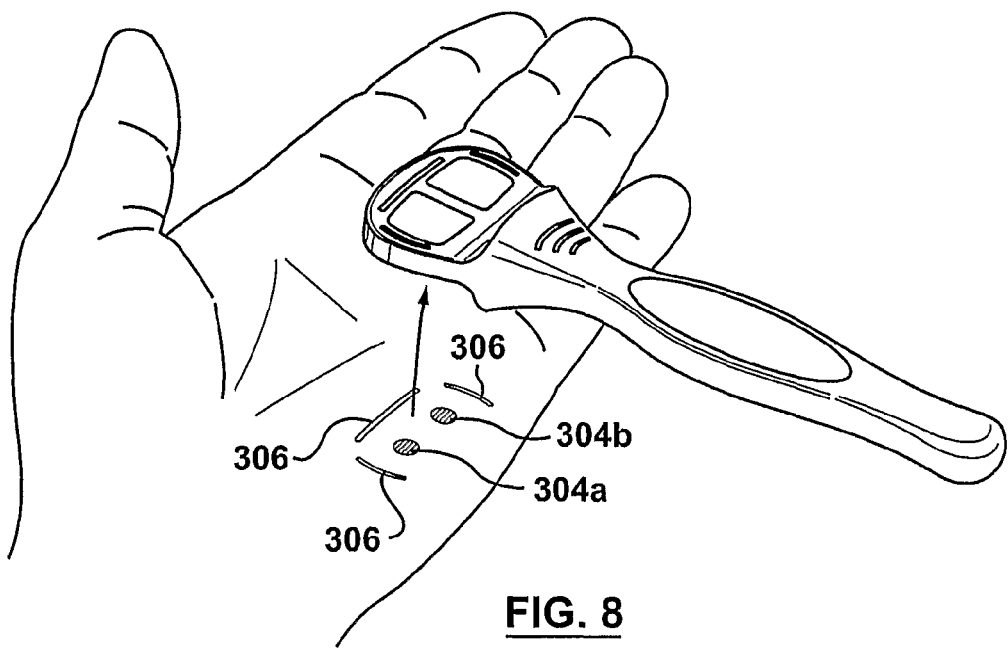
FIG. 8

DEVICE FOR APPLYING A DETECTOR REAGENT TO THE SKIN FOR MEASURING CHOLESTEROL

This application is a National Stage of International Application No. PCT/CA2006/000293, filed Feb. 28, 2006, which claims the benefit of Provisional Application No. 60/656,381, filed Feb. 28, 2005, the contents of which are herein incorporated by reference.

FIELD OF THE INVENTION

The present invention relates to a method and apparatus for non-invasive measurement of skin or skin tissue cholesterol. More particularly, the invention relates to the direct assay of cholesterol in skin samples, typically without using instrumentation, and as such is suitable for self-testing. In particular, one aspect of the invention provides for a device to apply a detector reagent to a selected area of skin. Another aspect of the invention provides for an indicator device to produce a visual change corresponding to the amount of detector reagent that is bound in the skin.

BACKGROUND OF THE INVENTION

Identifying people with high skin cholesterol is useful in determining individuals at risk of either having or developing atherosclerosis as well as those at risk of having similar or other diseases attributable to high cholesterol levels.

Coronary artery disease caused by atherosclerosis remains the number one cause of morbidity and mortality in North America and many other parts of the world. Prevention and intervention requires the cost effective identification of those individuals not only having the disease but also those at risk of developing the disease. Therefore, there is currently much interest in determining levels of marker molecules that are able to predict risk of atherosclerotic disease.

Measurement of blood plasma total cholesterol levels is one of the most widely used methods to determine risk of atherosclerosis. However, plasma total cholesterol levels alone do not accurately predict risk and better results have been obtained through measurement of plasma lipoproteins. Measurement of cholesterol in both low density lipoprotein (LDL) and high density lipoprotein (HDL) show advantages over measuring total cholesterol levels. All of these measurements require blood sampling after a long period of fasting so that dietary cholesterol does not interfere. Additionally, the sampling can be uncomfortable and carries some small risk of infection. Furthermore, the analysis often requires complicated and expensive equipment.

One example of a device that allows a user to obtain a blood cholesterol level is shown in U.S. Pat. No. 5,340,539. This patent circumvents some of the problems associated with visits to a doctor or clinic and makes fasting more convenient. However, a blood sample obtained from a finger prick with a lancet device is still required, which can be objectionable to many individuals.

In many cases, however, the levels of plasma cholesterol and lipoproteins do not correlate with the extent of atherosclerotic disease. It is therefore desirable to assay other marker molecules that reflect the extent of atherosclerosis and provide a risk assessment of cardiovascular disease.

For example, significant amounts of cholesterol occur in tissue in addition to that found in plasma and increased levels in tissue have been shown to play a major role in development of atherosclerosis. It has been demonstrated that the accumulation of cholesterol in tissues, including the skin, correlates closely with the amount of cholesterol found in arterial wall deposits. The measurement of cholesterol in skin, therefore, may reflect the extent of atherosclerosis. Indeed, cholesterol levels in skin biopsy samples have been shown to correlate with arteriosclerosis and to provide a risk assessment for patients with ischemic cardiac disease (Bouissou H., De Graeve J., et al. Ann. Biol. Clin. Vol 40, 364-365, 1982). Also, measurement of cholesterol extracted from lyophilized skin biopsy samples correlates with serum lipid quotient in normals and in patients with ischemic cardiac disease (Y. P. Nikitin et al. Kardiologiia, II, 48-51, 1987).

A drawback of obtaining skin biopsy samples for skin cholesterol determinations for risk assessment of atherosclerosis is that there can be pain in obtaining the skin samples. Moreover, a risk of infection at the biopsy site is possible. Obtaining the skin samples typically requires trained professionals. In addition, such samples contain subcutaneous fat and several layers of skin, some of which are highly vascularized. Consequently these samples contain heterogeneous sources of cholesterol and do not give reproducible and reliable cholesterol assay results.

One method for assaying various substances in the blood directly below the surface of the skin or on its surface is described in U.S. Pat. No. 4,458,686. This patent is based on electrochemical measurement of generated oxygen concentrations. For non-volatile substances that do not diffuse through the skin, however, it is necessary to implant enzymes under the skin to effect oxygen changes at the skin surface. The patent discloses the use of the enzyme cholesterol oxidase to determine cholesterol but it appears that it is blood cholesterol rather than skin cholesterol that is being measured.

Consequently, there is a need for a simple method and apparatus for non-invasive measurement of cholesterol in the skin that is unaffected by other sources of cholesterol.

SUMMARY OF THE INVENTION

The present invention provides a method and apparatus for non-invasive measurement of skin cholesterol. More particularly, one aspect of the invention provides for a device to apply a detector reagent to a selected area of skin. Another aspect of the invention provides for an indicator device to produce a visual change corresponding to the amount of detector reagent that is bound in the skin. The method and apparatus of this invention typically do not require any instrumentation for certain embodiments, allowing the invention to be suitable for self-testing, for example, but not limited to, in the home environment. As such the invention is particularly useful to allow individuals to assess their risk of atherosclerosis and related vascular diseases.

In one aspect of the invention, a method of measuring skin cholesterol is provided, the method comprising:

a) applying a detector reagent to a selected area of skin to bind to cholesterol present in the skin;

b) applying an indicator surface to the selected area of skin, the indicator surface having a solution that reacts with the detector reagent when the indicator surface is in contact with the selected area of skin, the reaction to produce a visual color change corresponding to the amount of detector reagent bound to cholesterol in the skin; and c) analyzing the color produced on the indicator surface to obtain a measurement of skin cholesterol.

The detector reagent can be applied to the selected area of skin using capillary action. In a preferred embodiment of the invention the detector reagent is applied to the selected area of skin by at least one wicking element. The wicking element can be saturated with detector reagent. In a preferred embodiment of the invention the wicking element is retained by a suitable applicator.

Moreover, the wicking element can deform a controlled amount to release the detector reagent.

The detector reagent concentration can be chosen so that a visual color change occurs in step b) when the cholesterol present in the skin is over a pre-selected threshold.

Further, the method can comprise applying the detector reagent by applying a control detector reagent and a test detector reagent to two separate areas of skin within the selected area of skin. The control detector reagent is a higher concentration of the test detector reagent. For this aspect, the test detector reagent concentration is chosen so that a visual color change occurs in step b) when the cholesterol present in the skin is over a pre-selected threshold.

Moreover, the method further comprises after step a) and before step b) removing any excess detector reagent not bound to the cholesterol in the skin. The excess detector reagent can be removed by a suitable absorbent media.

In addition, the indicator surface can include a substrate solution that reacts with a reporter component within the detector reagent. The indicator surface can be a pad of absorbent material saturated with a substrate solution, the substrate solution to react with the reporter component within the detector reagent.

Further, the method can comprise analyzing the color produced is by a reflectance spectrophotometer. Alternatively, the color produced is analyzed using a color comparator, such as, for example, but not limited to, a graded series of color bands.

In another aspect of the invention, a device to apply a detector reagent to a selected area of skin is provided, the device comprising:
  a) a body; and
  b) at least one applicator retained at one end thereof by the body and having a second end to contact a selected area of skin, the second end of the applicator to transfer to the selected area of skin a detector reagent.

The applicator preferably applies the detector reagent to the selected area of skin using capillary action. In one aspect the applicator includes a wicking element.

The body of the device can include at least one recess therein for receiving the one end of the wicking element. The recess is of a depth sufficient to receive therein the wicking element so that the second end of the wicking element does not extend beyond depth of the recess. Moreover, in a preferred embodiment of the invention, the perimetrical extent of a portion of the recess is greater than the perimetrical extent of the wicking element. The portion of the recess having the greater perimetrical extent surrounds the second end of the wicking element, preferably so that a gap is provided therearound.

In a preferred embodiment of the invention, the wicking element is a fiber plug. The wicking element can also be of inert polyolefin material.

Alternatively, the applicator can be a gel.

It is preferable that the applicator be cylindrical, however, where two applicators are provided, the applicators can be spaced from one another so that one applicator applies a control detector reagent and the second applicator applies a test detector reagent, and each applicator can present a different cross section at the second (or upper) end.

The applicator can be saturated with the detector reagent.

In a further aspect of the invention, an indicator device to produce a visual color change corresponding to an amount of detector reagent that is bound to cholesterol in the skin is provided. The indicator device comprises an indicator surface provided by a body of the device so that the indicator surface can contact a selected area of skin, the indicator surface containing a sufficient amount of a solution that reacts when contacted with a detector reagent that is bound to cholesterol in the selected area of the skin to produce a visual color change to at least a portion of the indicator surface.

The solution can be a substrate solution that reacts with a reporter component of the detector reagent.

The indicator surface can comprise an absorbent material, preferably, saturated with the solution. In one embodiment, the absorbent material is a pad. The pad can be woven, or, alternatively, of pressed fibrous sheet construction, or is constructed from hydrophilic material, or is a cellulose-based absorbent sheet, or is constructed from glass fiber material.

In a further aspect of the invention, an apparatus is provided for measuring skin cholesterol, the apparatus comprising:
  a) a body;
  b) at least one applicator retained at one end thereof by the body and having a second end to contact a selected area of skin, the second end of the applicator to transfer to the selected area of skin a detector reagent; and
  c) an indicator surface provided by the body so that the indicator surface can contact the selected area of skin, the indicator surface containing a sufficient amount of a solution that reacts when contacted with the detector reagent that is bound to cholesterol in the selected area of the skin to produce a visual color change to at least a portion of the indicator surface.

The applicator can apply the detector reagent to the selected area of skin using capillary action. In one embodiment, the applicator includes a wicking element.

Further the body can include an outer surface and at least one recess therein for receiving one end of the wicking element. In particular, the recess is of a depth sufficient to receive therein the wicking element so that the second end of the wicking element does not extend beyond the outer surface of the body. Moreover, the perimetrical extent of a portion of the recess is greater than the perimetrical extent of the wicking element, thereby allowing the recess to surround the second end of the wicking element, and, in a preferred embodiment, forming a gap therearound.

In one embodiment, the wicking element is a fiber plug. Alternatively, the wicking element is of inert polyolefin material.

In another embodiment, the applicator can be a gel.

The wicking element can be cylindrical, in a preferred embodiment. For embodiments, where two applicators are provided, the applicators can be spaced from one another so that one applicator applies a control detector reagent and the second applicator applies a test detector reagent. For this embodiment, each applicator can present a different cross section at the second ends thereof.

The applicator can be saturated with the detector reagent.

Moreover, the solution on the indicator surface can be a substrate solution that reacts with a reporter component of the detector reagent.

The indicator surface can comprise an absorbent material, which, in a preferred embodiment is saturated with the solution.

The absorbent material can be a pad, and the pad can be woven, or, alternatively, of pressed fibrous sheet construction, or is constructed from hydrophilic material, or is a cellulose-based absorbent sheet, or is constructed from glass fiber material.

In a preferred embodiment of the invention the body presents the at least one applicator and the indicator surface on opposite sides thereof.

Further the apparatus can comprise an absorbent media, the absorbent media provided on the body and spaced from the at least one applicator and the indicator surface. In one aspect, the absorbent media is constructed from hydrophilic material.

Further the apparatus can comprise at least one marker on a surface of the body that presents the at least one applicator, the at least one marker shaped to make an impression within the selected area of skin adjacent the area of skin that the detector reagent has been transferred to. The apparatus can therefore further comprise at least one of a second marker on the indicator surface, the at least on second marker corresponding in shape to the at least one marker.

In yet a further aspect of the invention, a kit for measuring skin cholesterol is provided, the kit comprising:
 a) a source of detector reagent;
 b) an applicator to apply the detector reagent to a selected area of skin;
 c) a source of a solution that reacts when contacted with the detector reagent; and
 d) an indicator surface to receive the solution so that when the indicator surface contacts the selected area of skin, the solution reacts with the detector reagent that is bound to cholesterol in the skin to produce a visual color change to at least a portion of the indicator surface.

The applicator of the kit preferably uses capillary action to apply the detector reagent to the selected area of skin. The applicator can include a wicking element, which can be a fiber plug, or, alternatively, is of inert polyolefin material. Further, the applicator can be a gel.

The kit can also provide two applicators, the applicators are spaced from one another so that one applicator applies a control detector reagent and the second applicator applies a test detector reagent. Each applicator can present a different cross section at the respective second ends thereof.

Further, the applicator can be the source of the detector reagent, and, preferably is saturated with the detector reagent.

Moreover, the solution can be a substrate solution that reacts with a reporter component of the detector reagent, which, preferably, is provided on the indicator surface, which can be an absorbent material. Further, in a preferred embodiment, the absorbent material is the source of solution. Further the absorbent material can be saturated with the solution.

In one aspect of the invention, the absorbent material of the kit can be a pad. The pad is woven, or, alternatively, the pad is of pressed fibrous sheet construction, or is constructed from hydrophilic material, or is a cellulose-based absorbent sheet, or is constructed from glass fiber material.

Further, the kit can comprise an absorbent media, and the absorbent media can be constructed from hydrophilic material.

Moreover, the applicator of the kit and the indicator surface can be provided on an apparatus on opposite sides thereof. Alternatively, the applicator, the indicator surface, and the absorbent media can be provided on an apparatus.

The kit can further comprise a reflectance spectrophotometer to analyze the color produced, or, alternatively, a color comparator to analyze the color produced, such as, but not limited to, a graded series of color bands.

Further, a method of applying a detector reagent to a selected area of skin to bind to cholesterol present in the skin is provided. The method comprising:

a) providing at least one applicator containing a sufficient quantity of detector reagent, the at least one applicator to transfer the detector reagent to a selected area of skin using capillary action; and
 b) contacting the selected area of skin with the applicator to wet the skin with detector reagent.

The detector reagent can be applied to the selected area of skin by at least one wicking element. Moreover, the wicking element can be saturated with detector reagent.

The wicking element deforms a controlled amount to release the detector reagent.

The wicking element can be retained by a suitable applicator.

In addition, the method of applying the detector reagent comprises applying a control detector reagent and a test detector reagent to two separate areas of skin within the selected area of skin. In one aspect, the control detector reagent is a higher concentration of the test detector reagent.

Further, the invention also provides for a method to produce a visual color change corresponding to an amount of detector reagent bound to cholesterol in the skin to measure skin cholesterol, the method comprising:

a) applying an indicator surface to a selected area of skin, the indicator surface having a solution that reacts with detector reagent when the indicator surface is in contact with the selected area of skin, the reaction to produce a visual color change corresponding to the amount of detector reagent bound to cholesterol in the skin; and
 b) analyzing the color produced on the indicator surface to obtain a measurement of skin cholesterol.

The indicator surface can include a substrate solution that reacts with a reporter component within the detector reagent. The indicator surface can be a pad of absorbent material saturated with a substrate solution, the substrate solution to react with a reporter component within the detector reagent.

The color produced can be is analyzed by a reflectance spectrophotometer, or, alternatively, using a color comparator, such as a graded series of color bands.

BRIEF DESCRIPTION OF THE DRAWINGS

For a better understanding of the present invention and to show more clearly how it would be carried into effect, reference will now be made by way of example, to the accompanying drawings that show a preferred embodiment of the present invention, and in which:

FIGS. 7 to 12 illustrate one embodiment of the method of this invention using the apparatus of FIG. 4; and FIG. 7a is cross-sectional view taken along the lines 7a-7a of FIG. 7.

DETAILED DESCRIPTION OF THE INVENTION

Figure 1:
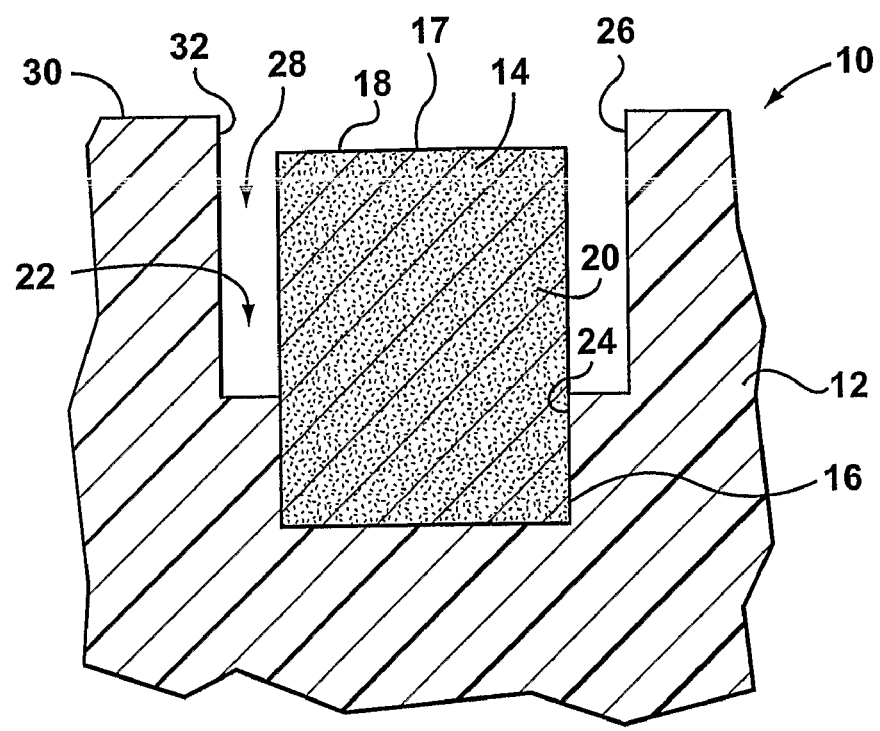
FIG. 1 is a cross-section of part of a device of the invention to apply a detector reagent to a selected area of skin.

The present invention provides a method and apparatus for non-invasive measurement of skin cholesterol. More particularly, one aspect of the invention provides for a device to apply a detector reagent to a selected area of skin. Another aspect of the invention provides for an indicator device to produce a visual change corresponding to the amount of detector reagent that is bound in the skin. The method and apparatus of this invention do not require any instrumentation allowing the invention to be suitable for self-testing, for example, but not limited to, in the home environment. As such the invention is particularly useful to allow individuals to assess their risk of atherosclerosis and related vascular diseases, as will hereinafter become apparent.

In general, the invention provides for a method of measuring skin cholesterol. The method includes: applying a detector reagent to a selected area of skin to bind to cholesterol present in the skin, the detector reagent including a reporter component; removing, when needed, the excess detector reagent by a suitable absorbent media; applying an indicator surface to the selected area of skin, the indicator surface having a solution that reacts with the reporter component when the indicator surface is in contact with the selected area of skin, the reaction to produce a visual color change corresponding to the amount of detector reagent with reporter component that is bound to cholesterol in the skin; and analyzing the color produced on the indicator surface to obtain a measurement of skin cholesterol.

It is to be realized that any area of skin can be used for testing, but the most suitable is that from the surface of the palm. Skin in the palm area does not have sebaceous glands whose secretions may contain cholesterol that could affect results. Also, the palm is particularly well suited for easy application and location by the apparatus of this invention, as will hereinafter be explained. The description that follows makes reference to the palm as the area of skin that is tested. However, it should be realized by those skilled in the art that the method is not restricted to use with the palm but can be applied to other areas of the skin.

Further, analysis of cholesterol on an area of the skin is achieved by using detector reagents that have specificity for cholesterol. Moreover, the detector reagents have a linked reporter component that generates a signal that is measurable when the reporter component is reacted with a suitable substrate solution.

Application of the detector reagent to the select area of the skin results in specific binding to cholesterol components present in the skin and concomitant binding of the reporter component. In one form of the assay the detector reagent is a compound of the type A-C-B; where A represents a specific cholesterol binding component, B is a reporter component, and C is a linking component. Reagents of this type are described in U.S. Pat. No. 5,489,510, the entirety of which is incorporated herein by reference.

The A component may be any agent that will discriminately bind to cholesterol in the skin. Examples of suitable agents include, but are not limited to, steroid glycosides, triterpene glycosides, hydrophobic proteins polyene antibiotics, and anti-cholesterol antibodies.

Compounds of the A-C-B type can be used where the B component is an enzyme. Examples of suitable enzymes include, but are not limited to, peroxidase, alkaline phosphatase, urease, galactosidase, glucose oxidase, and acetyl cholinesterase.

Further, suitable linking components C, that join the specific cholesterol binding component, A, to the reporter component, B, include, for example, but not limited to, zero-length cross-linkers, homobifunctional cross-linkers, and heterobifunctional cross-linkers. Zero-length cross-linkers mediate joining of the A and B molecules by forming a bond between them containing no additional atoms. Homobifunctional cross-linkers have two identical reactive groups that are used to join the A and B molecules and form a link between them having a variable number of atoms depending on the length of the particular homobifunctional agent used. Similarly, heterobifunctional cross-linkers have two different functional groups that are used to join the A and B molecules and form a link between them having a variable number of atoms depending on the length of the particular heterobifunctional agent used. The C component may also be a polymeric cross-linker which has multiple functional groups, either of the same type or of different types, and is able to link many molecules of A and B to a polymer backbone.

A particularly useful reagent of the A-C-B type is, for example, where A is digitonin, B is horseradish peroxidase, and C is a maleic anhydride-N-vinylpyrrolidone copolymer.

The devices and apparatus of the various aspects of the invention will now be described in more detail. The method of the invention using by way of example the devices and apparatus described herein will then follow.

Figure 2:
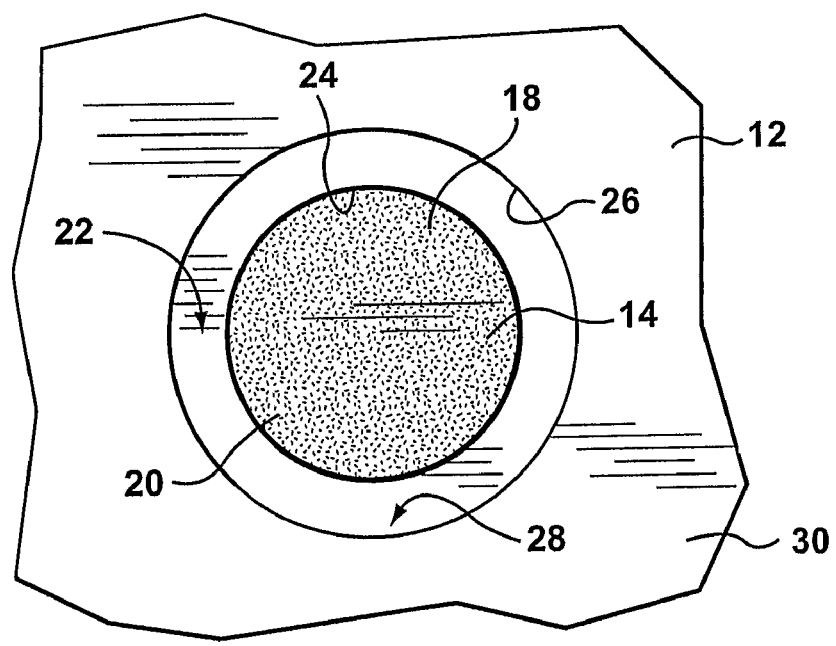
FIG. 2 is a top plan view of the device of FIG. 1.

FIGS. 1 and 2 illustrate a device to apply a detector reagent to a selected area of skin, according to one aspect of the invention. The device 10 includes a body 12 and at least one applicator 14. For purposes of FIGS. 1 and 2, only part of the body 12 is shown. It can be appreciated that the shape and configuration of the body can vary. Moreover, the body can feature various handle configurations (not illustrated) to allow a user to easily grip and use the device for the method of the invention.

The applicator 14 is retained at one end 16 (the lower end for the applicator shown in FIG. 1) by the body 12. A second end 18 (the upper end for the applicator shown in FIG. 1) of the applicator is provided to contact a select area of the skin (see FIG. 7a). Wetting of the selected area of the skin with a detector reagent is accomplished by the second end 18 of the applicator 14, as will hereinafter be described.

In the preferred embodiment of the invention, the applicator 14 transfers the detector reagent to the selected area of skin using capillary action. For self-testing, for example, in an at-home environment, a practical means of applying detector reagent to the skin of the operator is needed and which requires no measuring or other instrumentation. The inventor has found that a consistent application of detector reagent to a defined area of skin is achieved through the use of capillary action. For the embodiment illustrated in FIGS. 1 and 2, a wicking element 20 is used for the capillary action.

For the embodiment illustrated, body 12 includes a recess 22 to receive the applicator 14. In particular recess 22 has a lower portion 24 and an upper portion 26. End 16 of the applicator 14 can be shaped and configured to be retained in the lower portion 24 of the recess 22 by, for example, but not limited to, a friction fit.

The upper portion 26 of the recess 22 has a perimetrical extent greater than the perimetrical extent of the applicator 14. In particular, as illustrated, the upper portion 26 of the recess 22 within the body 12 surrounds the second end 18 of the applicator 14 so that a gap 28 in the form of an annular space is provided therearound.

In addition, the preferred embodiment features the applicator 14 recessed within the body 12 so that the contact surface 17 of the second end 18 of the applicator 14 does not extend any higher than surface 30 of the body.

In a preferred embodiment, the applicator 14 is saturated with the detector reagent to transfer the detector reagent to the skin upon contact. The transfer of the detector reagent must occur so as to wet an area of the skin upon contact and be relatively independent of pressure applied by the operator. Although saturating the applicator is preferred, it can be appreciated that it would be apparent to those skilled in the art that the applicator need not be saturated; however, it needs to contain a sufficient amount or quantity of detector reagent so as to wet an area of skin upon contact.

Various forms of applicators 14 can be used with this invention. For example the applicator can be a gel, or a fiber plug, which holds liquid through capillary action. Plugs of inert polyolefin material are useful since they are available in forms that are hydrophilic and thereby readily absorb aqueous based liquids like the detector reagent. Plugs having a reinforced wall and with fiber elements orientated longitudinally are useful since they have good axial strength, can readily conduct liquid along their axis, and transfer liquid to the skin upon contact.

In addition, applicator 14 can be of various cross-sectional shapes, widths and lengths. Cylindrical plugs are convenient to use as an applicator 14 since the diameter determines the area of detector reagent that is transferred to the skin and hence the area of the colored spot that is produced on the indicator surface, as will hereinafter be explained. For example, but not limited to, a suitable plug can have a diameter of about 3 mm to about 15 mm, and more preferably about 4 mm to about 10 mm diameter. In addition, the height of such a plug can be about 4 mm to about 10 mm.

As previously mentioned, the applicator 14 is preferably recessed within the body 12 so that the second end 18 of the applicator 14 does not extend any higher than surface 30 of the body 12. This addresses a need to limit the amount of force applied to the second end 18 of the applicator 14 by an operator when contacting the palm or other skin area. Too much force can expel excessive amounts of detector reagent and cause a large and uncontrolled area of the skin to be wetted. Conversely, too little force will result in poor contact with the skin and insufficient wetting of the skin. Therefore, there is a requirement to control the amount of pressure that is applied to an applicator yet maintain good contact with the skin.

In the preferred embodiment, this control is exercised by recessing the applicator 14 within the recess 22 of the body 12, as illustrated in FIG. 1, wherein the second end 18 of the applicator 14 is recessed just below the surface 30 of the body 12. The applicator 14 is can be, for example, but not limited to, recessed about 0.2 mm to about 2 mm, and more preferably from about 0.5 mm to about 1 mm. In this manner any excessive force applied by the hand and other skin area is transferred generally to the surrounding surface 30 of the body 12, and not to the applicator 14 (see FIG. 7a). In general, a portion of the skin and the underlying fleshy area are easily deformable and make suitable contact with the second end 18 of the applicator 14 when the applicator 14 makes contact with the select area of the skin. The fleshy part of the hypothenar area of the palm (see FIG. 7) is particularly suitable and readily deforms to make good contact with the second end 18 of the applicator 14.

The gap 28 or annular space can also prevent excess detector reagent from being squeezed uncontrollably onto the skin when the applicator 14 contacts the palm. Any excess pressure applied to the second end 18 of the applicator 14 might cause the applicator to deform outwardly. This will be accommodated by the gap 28, since applicator 14 is not restricted at its second end 18 by the walls 32 of the upper portion 26 of the recess 22.

Without gap 28, applying excess pressure to an applicator within a recess of the same diameter as the applicator would result in uncontrolled expulsion of excess detector reagent from the applicator resulting in excessive wetting of the skin. In effect the gap 28, or annular ring, represents a reservoir into which any excess detector reagent that is squeezed from the applicator can be retained. Gap 28 can be, for example, but not limited to, of about 0.2 mm to about 2 mm wide, with gaps of about 0.5 mm to about 1 mm being most preferable.

The dimensions provided above for the applicator are intended to be illustrative of an exemplary embodiment of the invention only, and it is to be understood that the invention is not to be limited to these dimensions, and that other shapes, configurations, and dimensions are contemplated by this invention.

Figure 3:
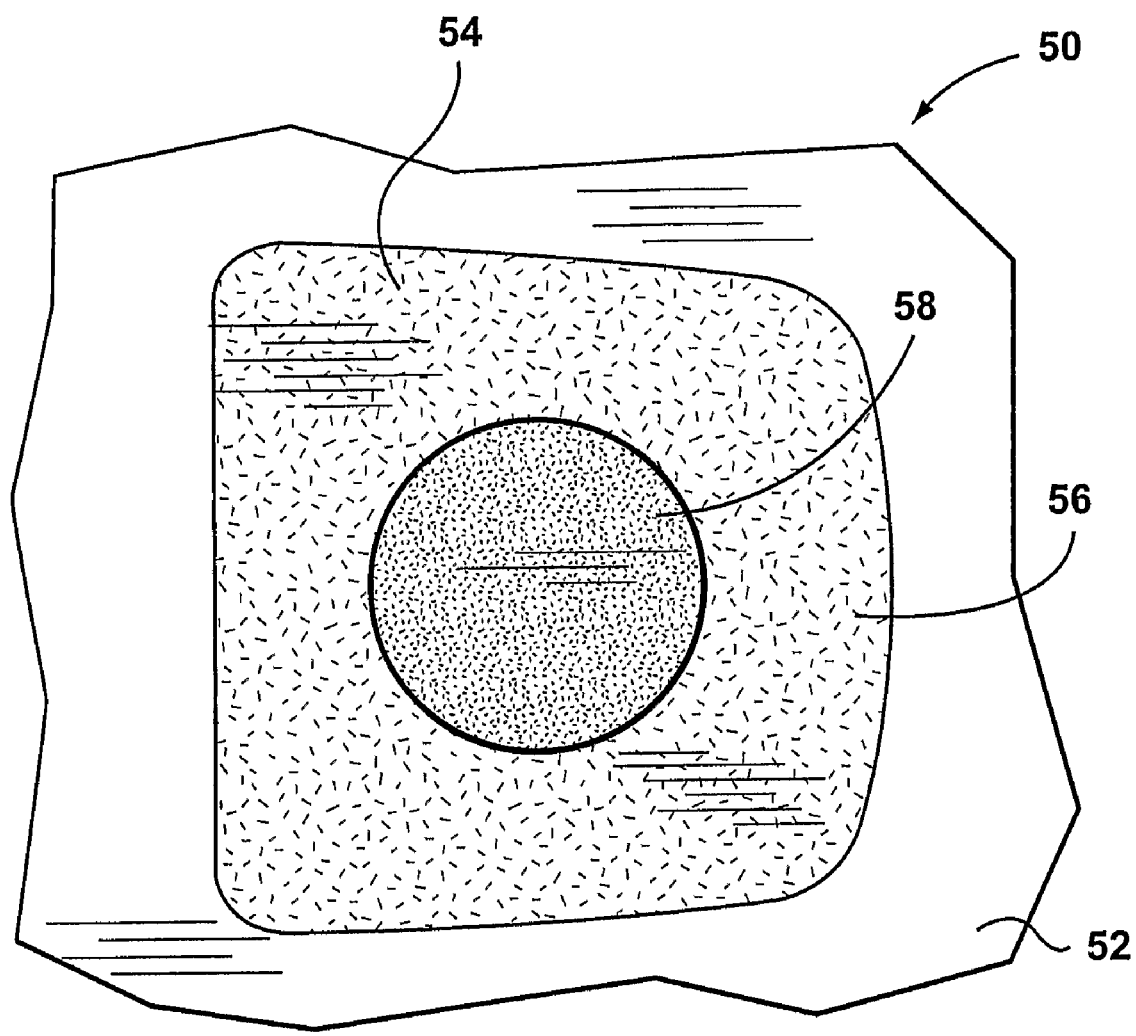
FIG. 3 is a top plan view of part of an indicator device of the invention.

FIG. 3 illustrates an indicator device 50 to produce a visual color change corresponding to an amount of detector reagent that is bound to cholesterol in the skin. The indicator device has a body 52 and an indicator surface 54 provided by the body 52. The indicator surface 54 is arranged on the body 52 so that it can contact the selected area of skin. Moreover, as will hereinafter be described, the indicator surface 54 contains a sufficient amount of a solution that reacts when contacted with the detector reagent that is bound to cholesterol in the selected area of the skin to produce a visual color change to at least a portion of the indicator surface.

In the embodiment illustrated in FIG. 3, the indicator surface 54 is an absorbent material in the form of a pad 56, preferably saturated with the solution, such as, for example, a substrate solution that reacts with the reporter component of the detector reagent. In particular, detection of specifically bound detector reagent is achieved through a substrate solution or signal-generating compound that reacts with the reporter component of the detector reagent. This is most conveniently achieved when the reporter component of the detector reagent is an enzyme and the substrate solution is a color-producing substrate for the enzyme. Horseradish peroxidase is a commonly used enzyme in these systems that utilize a peroxide substrate, such as hydrogen peroxide, in combination with a color producing redox reporter component.

In many clinical assays and immunoassays the enzyme component reacts with substrate in a fluid phase to produce a colored solution whose intensity can be measured spectrophotometrically. Alternatively, in assays where the enzyme reporter component is immobilized on a solid phase, such as an immunoblot assay, a precipitating color forming substrate solution is overlayed onto the immobilized enzyme. This generates a deposited colored product at the site of the bound enzyme.

In the method of the present invention the immobilized enzyme is bound to skin through a specific cholesterol binding component of the detector reagent and is not amenable to conventional detection methods using a substrate solution as is used for fluid phase and immunoblot assays described above.

In a novel aspect of the invention it was found that contacting a pad 56 of absorbent material having a sufficient quantity or amount of substrate solution (and preferably saturated with such solution) to the area of skin having the bound reporter component, results in color development. This color development is fluid phase in nature, but results in the development of color on the substrate pad in a manner similar to that produced in an immunoblot method. Soluble or insoluble, colored reporter component generated from the enzyme reaction is trapped in the interstitial spaces (not illustrated) of the pad 56 and diffuses only slowly, thereby forming a colored area.

The area of the color developed corresponds to the area of the enzyme detector that is immobilized on the applied skin. For example, when detector reagent is applied to the skin using the applicator 14 as described above having regard to FIGS. 1 and 2, then, as will become apparent from the more detailed description of the method to follow, a corresponding circular colored spot 58 is obtained on the pad 56.

In addition to generating a colored spot 58 that corresponds in area to the specifically bound detector, the intensity of the colored spot 58 correlates with the concentration of detector reagent used. The color intensity of the spots can be easily and conveniently measured using, for example, but not limited to, a reflectance spectrophotometer and recording the amount of color as chroma, reflectance or optical density.

Several types of materials are usable for pad 56 suitable to absorb the substrate solution. It can be appreciated that the material used in constructing the pad and the openness of the interstitial spaces affect how the substrate solution is absorbed and this in turn determines how well-defined a colored spot 58 is produced.

Thin, woven or pressed fibrous sheet materials are most suitable and hydrophilic materials are particularly useful for pads 56 employing aqueous based substrate solutions. Cellulose based absorbent sheets are readily available and when used as pads 56 produce good colored spots 58. Thin sheets of glass fiber material, as used for filters, are the most useful. Glass fiber is highly hydrophilic and the dense, tortuous capillaries of filter-grade material result in very well defined spots 58 that show little diffusion of color. Additionally, glass fiber is very white and provides a good background for display of the colored spots 58, particularly for spots that have low color intensity.

It is also desired to soak the pad 56 with a suitable substrate solution to generate good colored spots 58. For example, when the detector reagent is of the A-C-B type, with horseradish peroxidase as the enzyme component, then highly sensitive, commercially available substrate reagents can be used as the reporter component. These reporter components typically contain hydrogen peroxide and a benzidine-based, redox indicator dye such as 3, 3', 5, 5'-tetramethylbenzidine, and produce a blue colored reaction product with peroxidase enzymes. These liquid based reagents are particularly useful for soaking the pads 56 of the indicator device to subsequently generate colored spots.

It is known that dry reagent strips and pads incorporate an indicator dye, with or without a peroxide and are used to detect peroxidase or pseudo-peroxidase activity. One type of dry reagent pad employs a peroxidase reporter but without a peroxide component and is used for detection of hemoglobin (a pseudo-peroxidase) in feces. Hemoglobin is a marker for occult blood and the reagent pads are used in detection of colon cancer. In this system the redox reporter is usually guaiac, absorbed onto a porous matrix. Fecal material is applied to one side of the porous pad that is then sent for testing. At the testing site, hydrogen peroxide solution is applied to the second side of the pad where it diffuses through the matrix and reacts with any hemoglobin present. Subsequent reaction with the guaiac generates a blue colored reaction product indicative of the presence of hemoglobin. It will be appreciated by those skilled in the art that obviously, redox reporters for peroxidase other than guaiac can be used also in such pads and are included herein by extension.

A second type of dry reagent pad is used for detecting peroxidase activity e.g., urine dipsticks for detecting hemoglobin. Generally, these systems employ an organic hydroperoxide (e.g., cumene hydroperoxide, butyl hydroperoxide, or a similar compound) as well as a redox indictor dye (o-tolidene, 3,3',5,5'-tetramethylbenzidine or a similar redox indicator). A solution of these reagents along with stabilizer, buffer and other ingredients are absorbed onto a porous matrix and then dried to form a stable indicator pad. See for example U.S. Pat. Nos. 4,071,318 and 5,318,894, the entirety of which are incorporated herein by reference, which instruct in the methods of preparing such dry reagent materials.

In further aspects of the invention, both of the above types of dry reagent pads can be used as an indicator system for signaling peroxidative activity of detector reagent bound to skin cholesterol. In the first case a dry pad containing the guaiac or other peroxidative indicator, is wetted with dilute hydrogen peroxide solution and, in the method of the invention, the palm, having bound detector reagent, is applied to the wet pad. Peroxidase, specifically bound to cholesterol in the skin, causes a color change on the indicator pad that corresponds to the area of the bound detector.

In the second case the dry pad, containing both hydroperoxide and indicator is wetted with water. The palm, having bound detector reagent, is then applied to the wet pad. Detector reagent, specifically bound to cholesterol in the skin, causes a color change on the pad in an area that corresponds to the bound peroxidase.

In all instances, use of a substrate-soaked, absorbent pad 56, in accordance with this invention, avoids the direct application of liquid substrate solution to the skin and the very restrictive containment problems this could entail.

Figure 4:
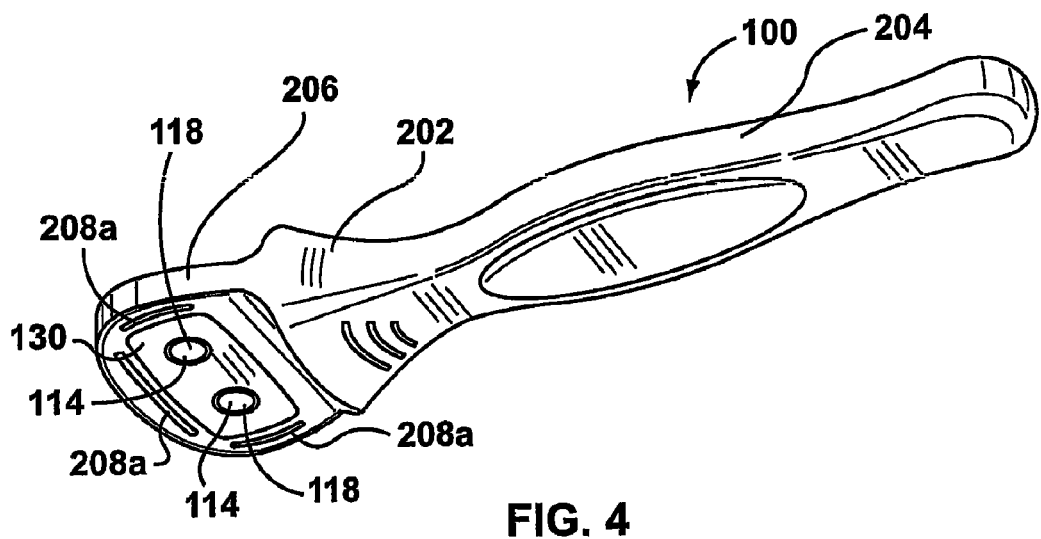
FIG. 4 is a perspective view of an apparatus of this invention including the device of FIG. 1 and the indicator device of FIG. 2.
Figure 5:
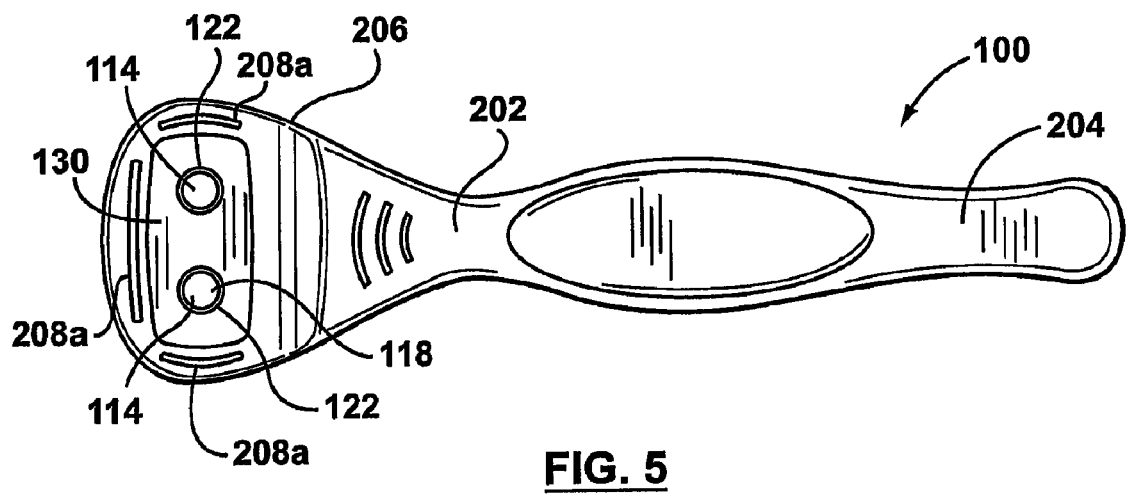
FIG. 5 is top plan view of the apparatus of FIG. 4.
Figure 6:
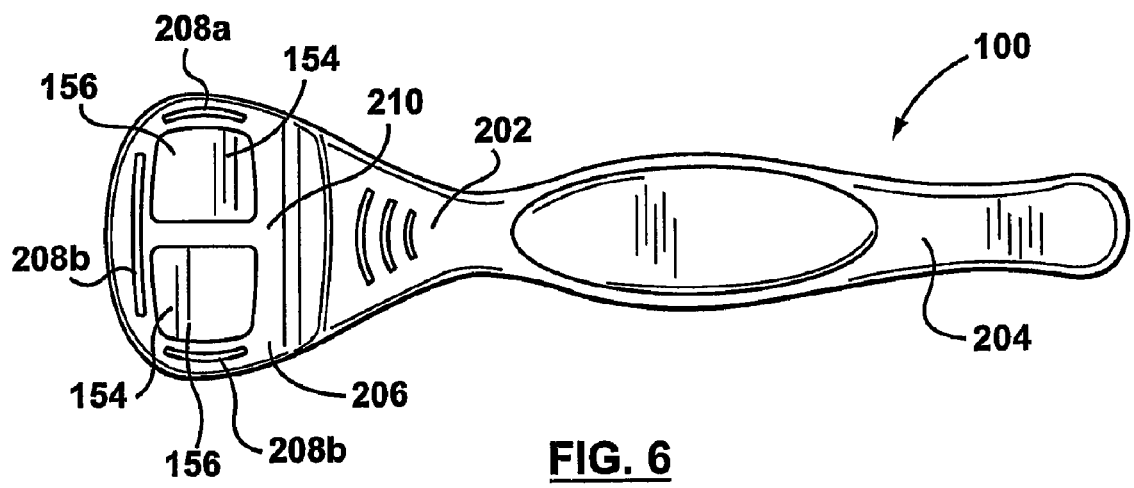
FIG. 6 is a bottom plan view of the apparatus of FIG. 4.

It can be appreciated that the device 10 for applying the detector reagent as illustrated in FIGS. 1 and 2, and the indicator device 50 illustrated in FIG. 3, can readily be combined into one apparatus 100, as best illustrated in FIGS. 4, 5, and 6. By combining the applicator 14 of device 10 with the indicator device 50 in a single apparatus 100, this invention allows for a relatively simple method for self-testing of cholesterol levels, particularly in, for example, but not limited to, an at-home environment.

Reference to apparatus 100 will be made using the same reference characters as used for the device 10, from FIGS. 1 and 2, and indicator device 50 from FIG. 3, but preceded with a "1." For example, in FIG. 4 where the applicator 14 of FIG. 1 is shown it is labeled 114, and in FIG. 6, where indicator surface 54 of FIG. 3 is shown it is labeled 154. New elements are introduced preceded by a "2," for example, apparatus 100 includes a body 202, featuring a handle 204 at one end, and at the other end thereof, a skin contacting portion (or end) 206 that carries the applicator 114, and the indicating surface 154. It is to be appreciated that apparatus 100 represents one illustrative embodiment combining the device 10 for applying the detector reagent and the indicator device 50. As illustrated apparatus 100 presents the applicator 114 on one side of end 206, and the indicator surface 154 on the opposite side thereof. Other configurations apparent to those skilled in the art are intended to be covered by this invention. For example, the apparatus 100 could also provide space for an additional absorbent media (not illustrated) to blot up excess detector reagent, when needed. The absorbent media can be spaced from the applicator and the indicator surface.

The description of device 10 for applying a detector reagent provided above having regard to FIGS. 1 and 2 applies to the description of apparatus 100 in so far as apparatus 100 is used to apply a detector reagent. In particular, apparatus 100 has at least one applicator 114 (two are shown for the embodiment illustrated), provided within a recess 122 (see FIG. 5). Moreover, the applicator 114 is recessed so that the second end 118 does not extend any higher than surface 130 of the body 202 of apparatus 100.

Surface 130 of apparatus 100 features a number of locator markers 208a spaced around a portion of end 206. The purpose of these markers is to leave an impression of the area of skin contacted by the apparatus 100 when applying the detector reagent, as will be hereinafter explained.

In a preferred embodiment of the invention apparatus 100 features two applicators 114 spaced from one another, as illustrated in FIG. 5. One of the applicators applies a control detector reagent to the area of skin, and the second applicator applies a test detector reagent. Although the embodiment of apparatus 100 as illustrated in FIGS. 4 and 5 show applicators 114 having the same cross-section, it can be appreciated that each applicator could present a different cross-section at the second end thereof for contacting the skin. This would allow for a quick visual check as to which is the control detector reagent and which is the test detector reagent.

Similarly, the description of indicator device 50 provided above and having regard to FIG. 3 applies to the description of apparatus 100 in so far as apparatus 100 is used as an indicator device. In particular, apparatus 100 has at least one indicator surface 154 (two are shown for the embodiment illustrated in FIG. 6). The indicator surface 154 can produce a visual color change corresponding to an amount of detector reagent that is bound to cholesterol in the skin once the indicator surface 154 contacts the selected area of skin. As previously discussed in relation to the indicator device 50 of FIG. 3, the indicator surface 154 is an absorbent material in the form of a pad 156, and preferably saturated with the solution, such as, for example, a substrate solution that reacts with the reporter component of the detector reagent applied by the applicators 114 of the apparatus 100.

Similarly, to the surface 130 of apparatus 100, surface 210 of end 206 features a number of locator markers 208b spaced therearound. The purpose of these markers is to match the corresponding impressions in the area of skin left by markers 208a when applying the detector reagent, so that the pads 156 can overlay the same area of skin, as will be hereinafter explained.

In a preferred embodiment of the invention apparatus 100 features two pads 156, spaced from one another, as illustrated in FIG. 6. Each pad 156 corresponds to one of the applicators 114. It is to be appreciated, however, that one pad can be provided sized to encompass an area similar to the area of the two pads 156 shown for the apparatus 100. Other shapes and configurations for the pads can also to be contemplated by those skilled in the art.

It can be appreciated that for testing purposes the area of skin can contact both the control detector reagent and the test detector reagent, each detector reagent applied by the separate applicators 114. In practice, the same detector reagent is used with both applicators; a high concentration of detector reagent is used in the control, however. The high concentration of control detector reagent is chosen such that after subsequent development on the indicator surface 154, all individuals tested, irrespective of their skin cholesterol level, will produce a clearly visible colored spot. Giving a readily distinguishable colored spot with the control detector assures the individual that the area of skin, for example, the palm, has made sufficient and good contact with the detector reagents.

The applicator transferring the test detector reagent contains a lower concentration of the same detector reagent as the control detector reagent. The test detector reagent concentration is chosen such that after development on the indicator surface, a colored spot is produced whose intensity reflects the level of cholesterol in the skin.

In another aspect of the invention the detector reagent concentration is chosen such that individuals with a set threshold level of skin cholesterol will produce no colored spots on the indicator surface. Individuals with skin cholesterol levels above this threshold level will produce a spot whose intensity reflects their skin cholesterol level. In this manner a simple test is provided to identify individuals with a skin cholesterol level above a selected value (i.e., a discernable colored spot is produced), and therefore is deemed to be above a pre-selected threshold amount that places them at an increased risk for atherosclerosis and other related cardiovascular disease.

In another aspect of the invention the detector reagent concentrations can be chosen so that all individuals tested give a colored spot and whose intensity is proportional to their skin cholesterol level. Individuals with high levels of skin cholesterol will bind more detector reagent in a given contact time than individuals with low levels of skin cholesterol and the color developed will be proportional to the amount of detector bound. In this type of assay the intensity of the colored spot can be matched up to one of several prescribed colors on a color comparator card, as will hereinafter be described. The color of the spot produced enables an individual's skin cholesterol to be semi-quantitatively determined and then assigned to one of several risk groups, for example, low, normal and high.

More accurate determination of the intensity of the colored spots developed with these assays can done using instruments that measure the amount of color. For instance, simple reflectance spectrophotometers can be used and color attributes such as chroma, reflectance, and optical density can be used to determine the amount of color, as described in international patent application, publication No. WO 01/011359 A3, the entirety of which is herein incorporated by reference.

The method of the invention will now be described in detail making reference to FIGS. 7, 7a, 8, 9, 10, 11, and 12, and using, for purposes of illustration, the apparatus 100 of the invention. It can be appreciated, however, that the same method can be practiced using, for example, a separate device 10 and indicator device 50 and applying the following steps.

First, apparatus 100 is used to apply detector reagents to a Selected area of skin, for example, palm 300. For this example, the applicators 114 are two round, absorbent, polyolefin filters 114a and 114b, 5 mm in diameter and 5 mm long and these are available from Filtrona Inc (Richmond, Va.). The filters are inserted into an injection molded polypropylene cartridge unit that allows the filters to be held by a friction fit in the cartridge and positions the second end 118 about 0.5 mm below the surface 130 of the apparatus. In addition the second end 118 of each filter is surrounded by an annular space about 0.75 mm wide. Each filter is saturated with a detector reagent of an A-C-B conjugate of digitonin (A) and horseradish peroxidase (B) linked to a maleic anhydride-N-vinylpyrrolidone copolymer (C). One filter 114a, is designated as a positive control, is saturated with a high concentration of detector reagent and the second filter 114b, is designated as a test filter, is saturated with a lower concentration of detector reagent. Typically, the positive control will have detector reagent at about 50-100 ug/mL, and the test detector reagent at about 1-10 ug/mL.

The hypothenar area of the palm 300 is selected, cleaned, dried and then placed on the end 206 of the apparatus 100 so as to make contact with detector reagents on the applicators 114a and 114b. This allows the detector reagents to bind to cholesterol in the skin as shown at 304a and 304b in FIG. 8, wherein 304a represents the control detector reagent from applicator 114a, and 304b represents the test detector reagent from applicator 114b. Alternatively, the apparatus can be placed into contact with the palm 300. After contact with the applicators 114a and 114b for about one minute, the palm 300 and apparatus 100 are separated, as shown in FIG. 8. Also as shown in FIG. 8, markers 208a leave impressions 306 in the palm 300, outlining the area of the skin that the detector reagents have been applied to. If desired, the markers 208a can be labels that impress into the skin suitable words, such as "control" or "test" that are impressed into the skin beside 304a and 304b, respectively, where the control detector reagent and the test detector reagent are bound to cholesterol in the skin.

Figure 9:
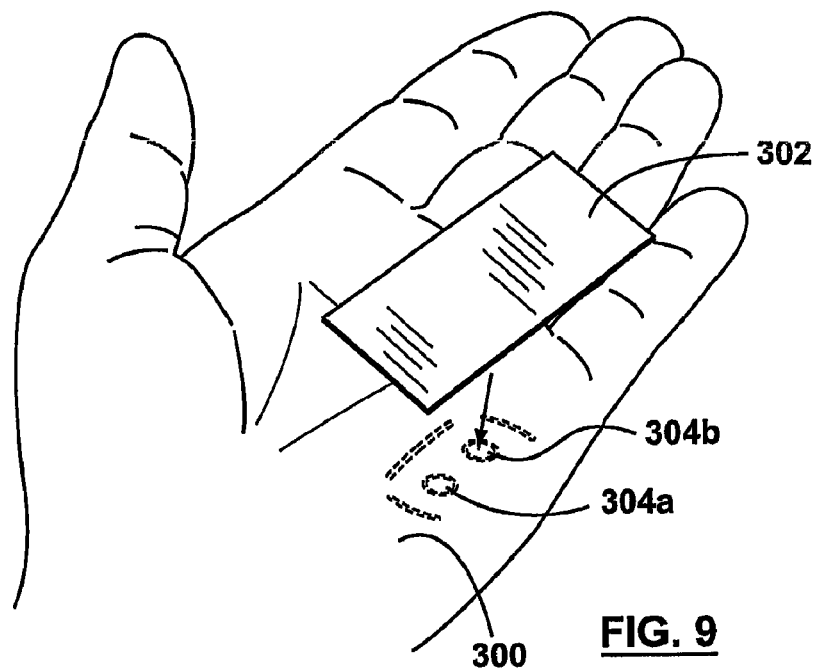

If there is any excess unbound detector reagent, this is removed by immediately applied an absorbent media or blotting pad 302 as shown in FIG. 9. Two further blotting steps can be done by applying the palm to fresh areas of the cellulose material. All blotting steps are carried out by applying firm pressure on the hypothenar area of the palm 300 with the blotting pad 302. It has been found that while a single blotting application of the skin removes almost all of the non-specifically bound detector, three applications is the most convenient to remove the excess. More than three applications is usually unnecessary and does not remove any more of the non-specifically bound detector.

Removing excess unbound detector, if present, is necessary since only the specifically bound detector generates a meaningful signal. Washing is an alternative and equivalent means of removing the non-specifically bound detector reagent but is less convenient for use in a simple, rapid test where the steps follow in sequence and are carried out by an apparatus, such as apparatus 100 of this example.

Any of various types of absorbent media 302 are suitable as a blotting material. Highly absorbent woven hydrophilic materials such as cotton or cellulose based tissues are particularly well suited. Disposable kitchen-towel and other similar common sheet stock are preferred and materials that leave no lint residue on the palm are most preferred.

As previously mentioned in relation to the discussion of apparatus 100, the absorbent media 302 can be part of the apparatus adjacent to the surface 130 that holds the applicators 114. In this manner it is a simple procedure after applying detector reagents, to transfer the palm to the absorbent media 302 for removal of non-specifically bound detector. In another form of the method, and as illustrated in FIG. 9, the absorbent media is separate from the apparatus used to apply the detector reagents and the palm is then moved to the isolated absorbent media 302 for the blotting step.

Figure 10:
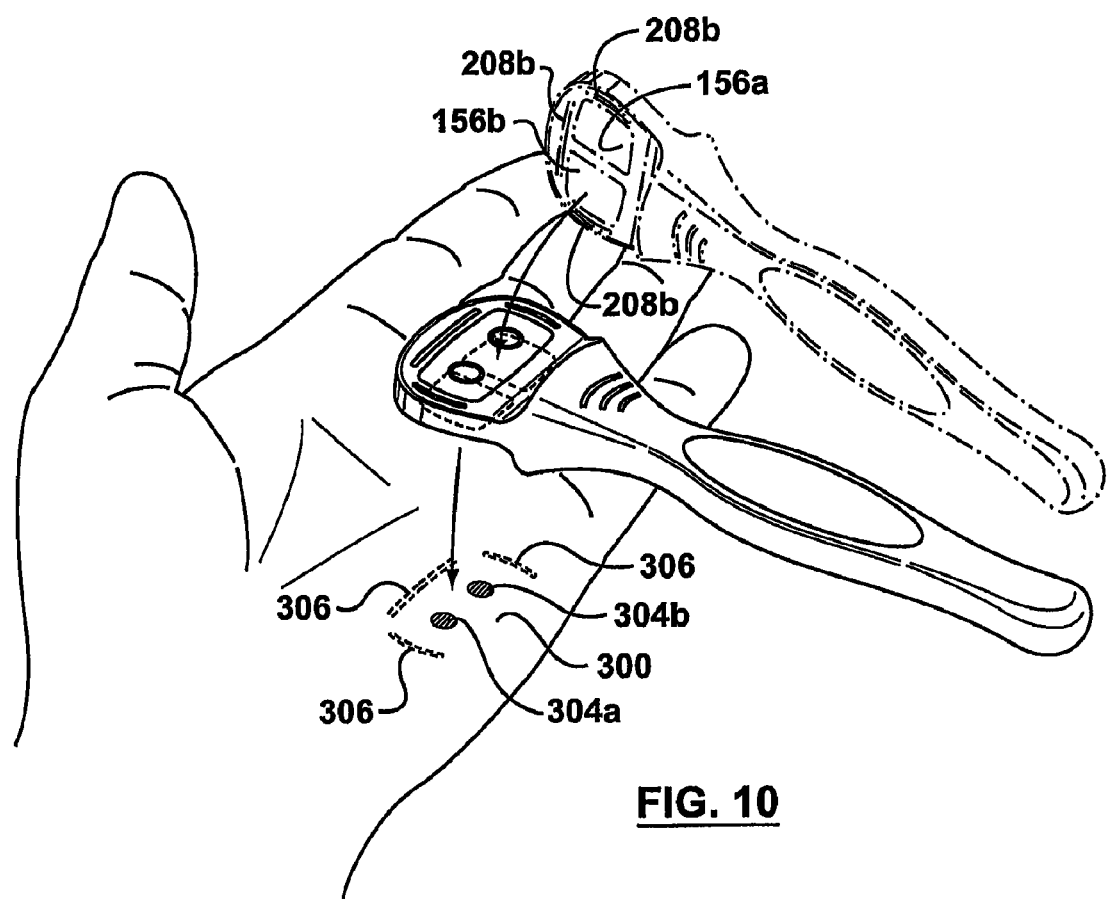

The hypothenar palm area 300, having specifically bound detector reagent, is then placed onto a freshly prepared pad 156, such as pads 156a and 156b, illustrated in FIG. 10, saturated with a substrate solution. Fiberglass material 934 AH (Whatman Inc.) and K-Blue Max substrate solution (Neogen Corp.) are typically used. Alternatively, the apparatus 100 can be brought into contact with the palm 300. In either situation, the pads 156a and 156b must align over where the detector reagents bind to cholesterol in the skin as shown at 304a and 304b. respectively, in FIG. 8. Accordingly, markers 208b on side 210 of end 206 of apparatus 100 are used to align end 206 with the impressions 306 left on the palm 300 by markers 208a.

Figure 11:
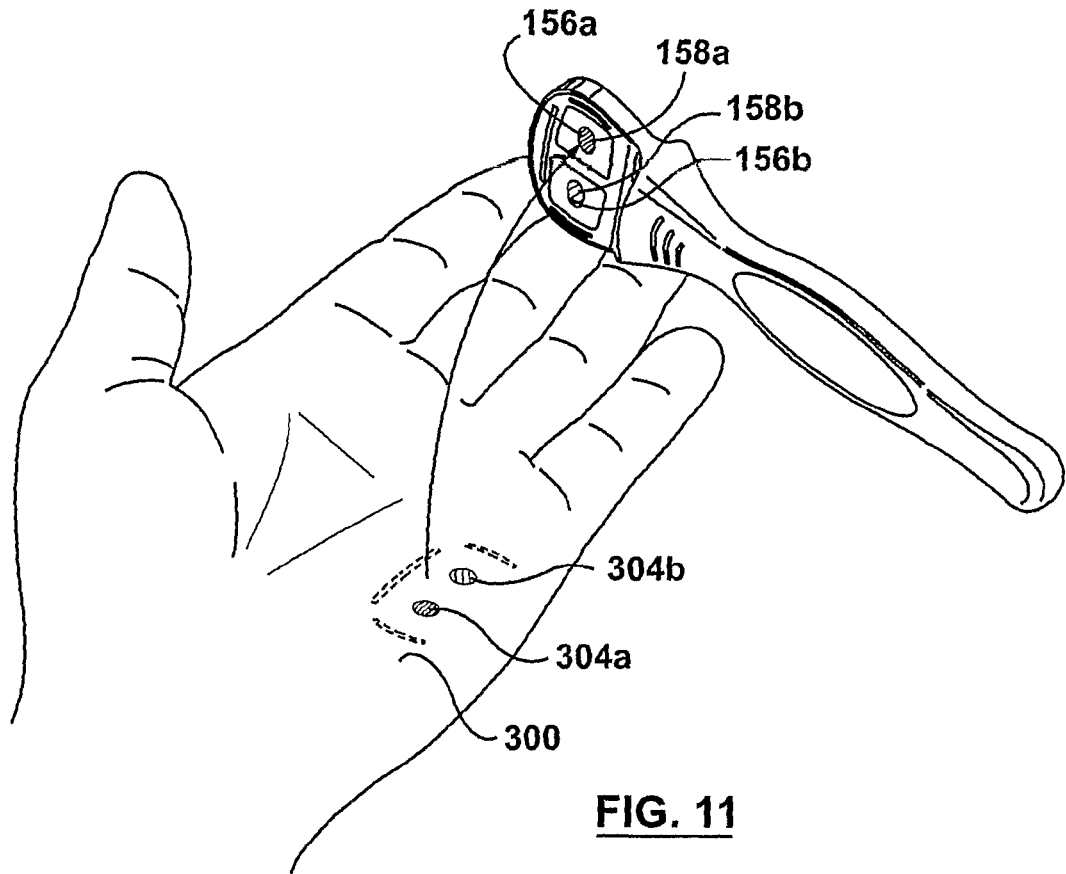

After contact with the substrate solution on the pads 156a and 156b for about one minute the palm is removed, as shown in FIG. 11.

On removing the palm 300 from the pads 156a and 156b there will be one or two round, blue spots 158a and 158b, respectively, of approximately 5 mm diameter on the pads. These spots, 158a and 158b correspond to where the detector reagents from the applicators 114a and 114b were bound to the palm as at 304a and 304b, respectively.

All individuals will have a blue spot in the position that corresponds to the positive control applicator. If a low threshold concentration of detector is used in the test applicator a second spot may or may not be visible depending on the skin cholesterol level of the individual tested. Individuals with low or normal levels of skin cholesterol will not give a second test spot, while individuals with high levels of skin cholesterol will develop a second spot.

Figure 12:
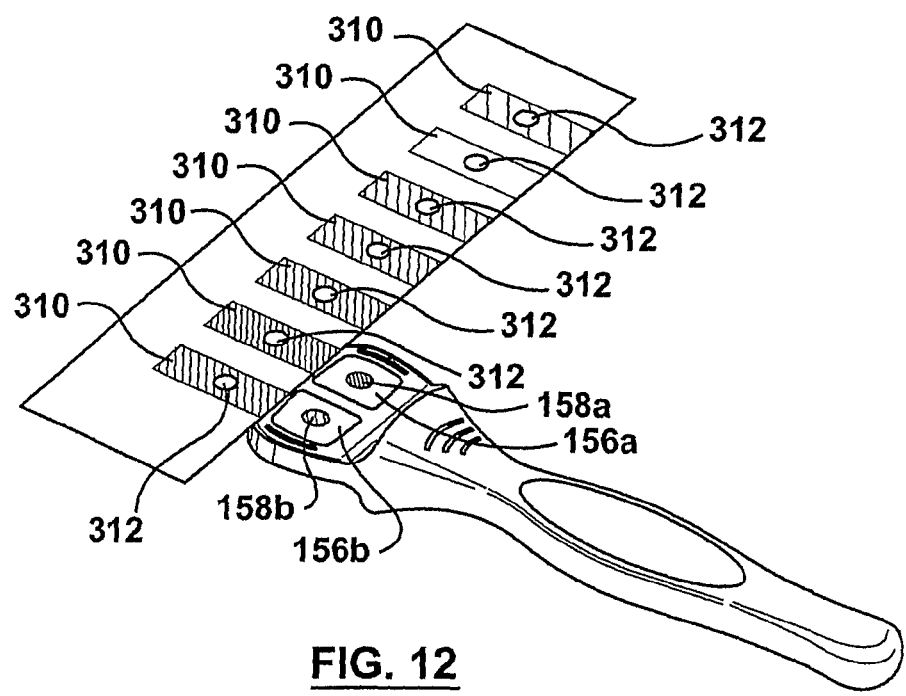

If a non-threshold level of detector is used in the second test applicator, then all individuals will produce two blue spots. In addition to a strong blue positive control spot a second blue spot of variable intensity will be seen. The intensity of this second spot will depend on the skin cholesterol level of the individual being tested and a measure of the intensity can be made using a color comparator card 308, as shown in FIG. 12.

The intensity of the color of the test spot is measured with the color comparator card 308 having bands 310 of blue dye of variable intensity. In one embodiment, each band can have a hole 312 of about 4 mm in diameter in its centre. In this embodiment, the comparator card 308 can be guided over the test spot 158b on the pad 156b so that the test spot shows up in the hole 312 in the centre of each band 310 of color. The hole 312 in each band 310 is placed in turn over the test spot until a matching intensity between the test spot and a surrounding colored band 310 is achieved.

Each colored band 310 can be given a score that reflects a risk factor based on a corresponding skin cholesterol level. Individuals with a high skin cholesterol level will develop a more intense blue spot, obtain a higher score and have an increased risk of either having or developing atherosclerosis as well as those at risk of having similar or other diseases attributable to high cholesterol levels.

While the range of skin cholesterol levels in the normal and at-risk population determines the intensity of the bands 310 on the comparator cards 308, the color of the bands 310 is determined by the substrate solutions used. With 3, 3', 5, 5'-tetramethylbenzidine substrate the spots developed are an aqua blue. A suitable and appropriate color comparator is prepared based on the range of hues and chromas developed using this substrate. For other substrates different colors are developed and corresponding comparator cards are required.

Incorporation of background base colored dyes in the pads 156a and 156b can allow the range of colors developed to be varied as well as intensities. With dry reagent pads a yellow or orange colored dye can be incorporated with a blue producing indicator. At low levels of substrate conversion the colored spots remain yellow or orange, at intermediate levels the spots are greenish and at high levels the spots are greenish-blue. This allows variable color comparisons to be done in place of intensity comparisons and may provide an alternative and advantageous reading of developed spots.

It can be appreciated that although the method of the invention has been described using an apparatus 100, a number of alternative devices can be used, such as a separate device for applying the detector reagents and a separate indicator device. Accordingly, the invention is readily adaptable to a kit suitable for self-testing skin cholesterol, particularly, for example, but not limited to, in an at-home environment.

The kit would include a source of detector reagent; an applicator to apply the detector reagent to a selected area of skin; a source of a solution that reacts when contacted with the detector reagent; and an indicator surface to receive the solution so that when the indicator surface contacts the selected area of skin, the solution reacts with the detector reagent that is bound to cholesterol in the skin to produce a visual color change to at least a portion of the indicator surface.

It can be appreciated that the applicator in the kit can be the same as found in device 10, or in apparatus 100, as previously described. In particular, in the preferred embodiment, the applicator is the source of the detector reagent (i.e., it has previously been saturated with the detector reagent). However, it is contemplated by this invention that the kit might include the detector reagents separately, and therefore the user would have to soak the applicator.

Similarly, the indicator surface in the kit can be the same as found in device 50 and 100 as previously described. Therefore the indicator surface can be the source of solution (i.e., previously soaked with the substrate solution). However, again, it is contemplated by this invention that the kit might include the substrate solutions separately, and therefore the user would have to soak the indicator surface (pads).

Further, the kit of this invention can also include an absorbent media for the blotting step, when needed.

As previously described, for example apparatus 100, the applicator and the indicator surface can be provided on the same apparatus (for example, on opposite sides thereof and included in the kit combined as such.

Moreover, the kit can provide the applicator, the indicator surface, and the absorbent media on the same apparatus.

Finally, the kit can provide some means to analyze the color produced when the method is carried out. For example, the kit can include a color comparator to analyze the color produced. The color comparator can be a graded series of color bands, as previously described. Alternatively, the kit can include a reflectance spectrophotometer to analyze the color produced.

The following description is meant to be illustrative only and not limiting. Other embodiments of this invention will be apparent to those of ordinary skill in the art in view of this description.

While the embodiments of the invention disclosed are presently considered to be preferred, various changes and modifications can be made without departing from the scope of the invention. The disclosure is intended to be illustrative and not exhaustive. This description will suggest many variations and alternatives to one of ordinary skill in this art. All these alternatives and variations are intended to be included within the scope of the claims. Those familiar with the art may recognize other equivalents to the specific embodiments described that are also intended to be encompassed by the claims.

I claim:

1. A device to apply a detector reagent to a selected area of skin to detect an analyte, the device comprising:
   a) a body; and
   b) at least one applicator retained at a first end thereof by the body and having a second end to contact a selected area of skin, the second end of the applicator being adapted to transfer to the selected area of skin a detector reagent to detect an analyte;
   wherein the body includes at least one recess therein for receiving the detector reagent,
   wherein the recess is of a depth sufficient to receive therein the applicator so that the second end of the applicator does not extend beyond the recess, and
   wherein the body, the recess, and the applicator remain in a fixed position relative to each other.

2. The device of claim 1, wherein the applicator applies the detector reagent to the selected area of skin using capillary action.

3. The device of claim 1, wherein the applicator includes a wicking element.

4. The device of claim 1, wherein a perimetrical extent of a portion of the recess is greater than a perimetrical extent of the wicking element.

5. The device of claim 4, wherein the portion of the recess having the greater perimetrical extent surrounds the second end of the wicking element.

6. The device of claim 5, wherein the portion of the recess having the greater perimetrical extent surrounds the second end of the wicking element so that a gap is provided therearound.

7. The device of claim 3, wherein the wicking element is a fiber plug.

8. The device of claim 3, wherein the wicking element is of inert polyolefin material.

9. The device of claim 1, wherein the applicator is a gel.

10. The device of claim 1, wherein the applicator is cylindrical.

11. The device of claim 1, wherein two applicators are provided, the applicators are spaced from one another so that a first applicator applies a control detector reagent and a second applicator applies a test detector reagent, wherein said test detector reagent detects the analyte or levels of the analyte on said selected area of skin.

12. The device of claim 11, wherein each applicator presents a different cross section at said second end.

13. The device of claim 11 wherein said first applicator has a low concentration of detector reagent and said second applicator has a high concentration of detector reagent.

14. The device of claim 1, wherein the applicator is saturated with the detector reagent.

15. The device of claim 1, wherein the detector reagent is adapted to detect levels of skin cholesterol.

16. The device of claim 1 wherein said first end of the body has a first side and a second side opposite said first side, and wherein said applicator is located on said first side and a pad is located on said second side.

17. The device of claim 16 wherein said applicator comprises a detector reagent and said pad comprises a substrate solution.

18. The device of claim 17 wherein two applicators are provided, the applicators are spaced from one another so that a first applicator applies a control detector reagent and a second applicator applies a test detector reagent, wherein said test detector reagent detects the analyte or levels of the analyte on said selected area of skin.

19. The device of claim 18 wherein two applicators are provided, the applicators are spaced from one another so that a first applicator applies a control detector reagent and a second applicator applies a test detector reagent, wherein said test detector reagent detects an analyte or levels of an analyte on said selected area of skin.

20. The device of claim 17 wherein said detector reagent and substrate produce a visual color change.

* * * * *